United States Patent [19]

Galindo

[11] Patent Number: 5,261,878
[45] Date of Patent: Nov. 16, 1993

[54] DOUBLE BALLOON PEDIATRIC DUCTUS ARTERIOSUS STENT CATHETER AND METHOD OF USING THE SAME

[75] Inventor: Alvaro Galindo, Tarzana, Calif.

[73] Assignee: The Regents of the University of California, Oakland, Calif.

[21] Appl. No.: 885,946

[22] Filed: May 19, 1992

[51] Int. Cl.$^5$ ............................................. A61M 29/00
[52] U.S. Cl. ........................................ 604/96; 606/194
[58] Field of Search ................................. 604/96–101, 604/53, 54, 55; 606/194

[56] References Cited

U.S. PATENT DOCUMENTS

| | | | |
|---|---|---|---|
| 4,456,011 | 6/1984 | Warnecke | 604/101 |
| 4,741,328 | 5/1988 | Gabbay | 604/99 |
| 4,771,765 | 9/1988 | Choy et al. | 604/101 X |
| 4,794,928 | 1/1989 | Kletschka | 604/101 X |
| 4,976,692 | 12/1990 | Atad | 604/101 |

OTHER PUBLICATIONS

Transluminally-Placed Endarterial Crafts—Dotter—Investigative Radiology Sep.-Oct. 1967 vol. 4, pp. 329-332.
Intravascular Stents and Transluminal Angioplasty—Sigwart et al.—New England Journal of Medicine, Mar. 19, 1987, pp. 701-706.
Expandable Intraluminal Graft: A Preliminary Study—Palmaz et al.—Radiology Jul. 1985, pp. 73-77.
Atherosclerotic Rabbit Aortas: Expandable Intraluminal Grafting—Palmaz et al.—Radiology 1986; 160:723-726.
Expandable Intraluminal Vascular Graft: A Feasibility Study—Palmaz et al.—Surgery Feb. 1986, pp. 199-205.
Expandable Intrahepatic Portacaval Shunt Stents: Early Experience in the Dog—Palmaz et al—AJR 145:821-825, Oct. 1985.
Balloon-Expandable Intravascular Stent—Palmaz et al.—AJR 150:1263-1269, Jun. 1988.
Use of Endovascular Stents in Congenital Heart Disease—O'Laughlin et al.—Circulation 1991;83:1923-1939.
A Novel Method to Maintain Ductus Arteriosus Patency—Coe et al.—J Am Coll Cardiol 1991;18:837-841.
Use of Intravascular Endoprothesis . . . —Moore et al.—JACC vol. 17. No. 2, Feb. 1991:19A.
Redilating Ductal Stents in Newborn Lambs—Coe et al.—Abstracts From the 64 Scientific Sessions, II-545.
Introduction to Intravascular Stents—Richard A. Schatz—Cardiology Clinics—vol. 6, No. 3, Aug. 1988.

Primary Examiner—John D. Yasko
Attorney, Agent, or Firm—Daniel L. Dawes

[57] ABSTRACT

A cardiac catheter for use in maintaining the patency of the ductus arteriosus in infants is provided with two inflatable balloons, a distal end balloon and a stent balloon. Each balloon is independently inflatable. The stent is carried temporarily on the stent balloon and is delivered by the catheter to the site of the ductus arteriosus. Expansion of the stent balloon expands the stent and places it at the target site. The stent balloon is confidently and reliably placed in the ductus arteriosus by first inflating the distal end balloon and withdrawing the catheter until abuts the opening of the ductus arteriosus through which it has been previously disposed. When this abutment is realized, the stent balloon is necessarily positioned appropriately within the ductus arteriosus. While maintaining the inflation of the distal end balloon, the stent balloon is inflated and the stent placed. After placement, both the distal end balloon and stent balloon are deflated and the catheter withdrawn.

20 Claims, 2 Drawing Sheets

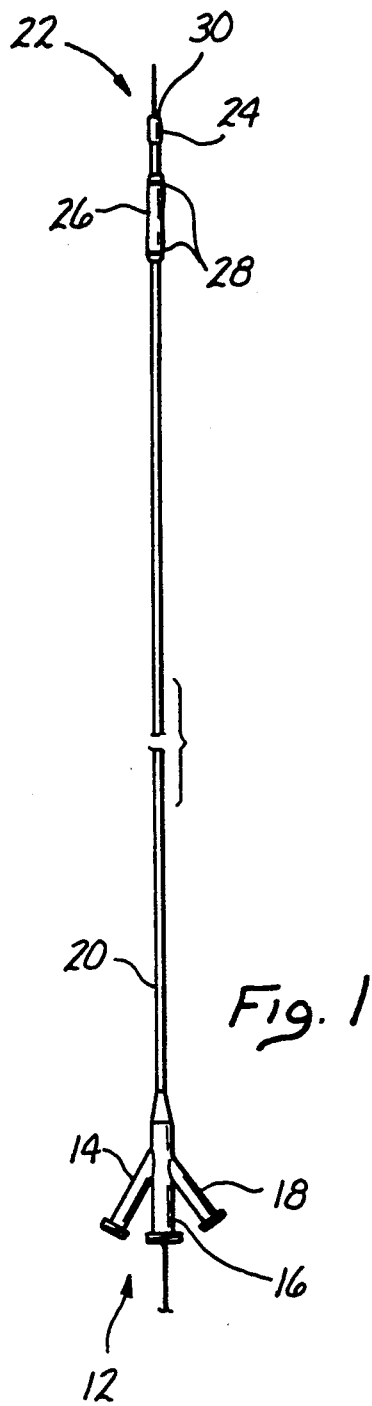
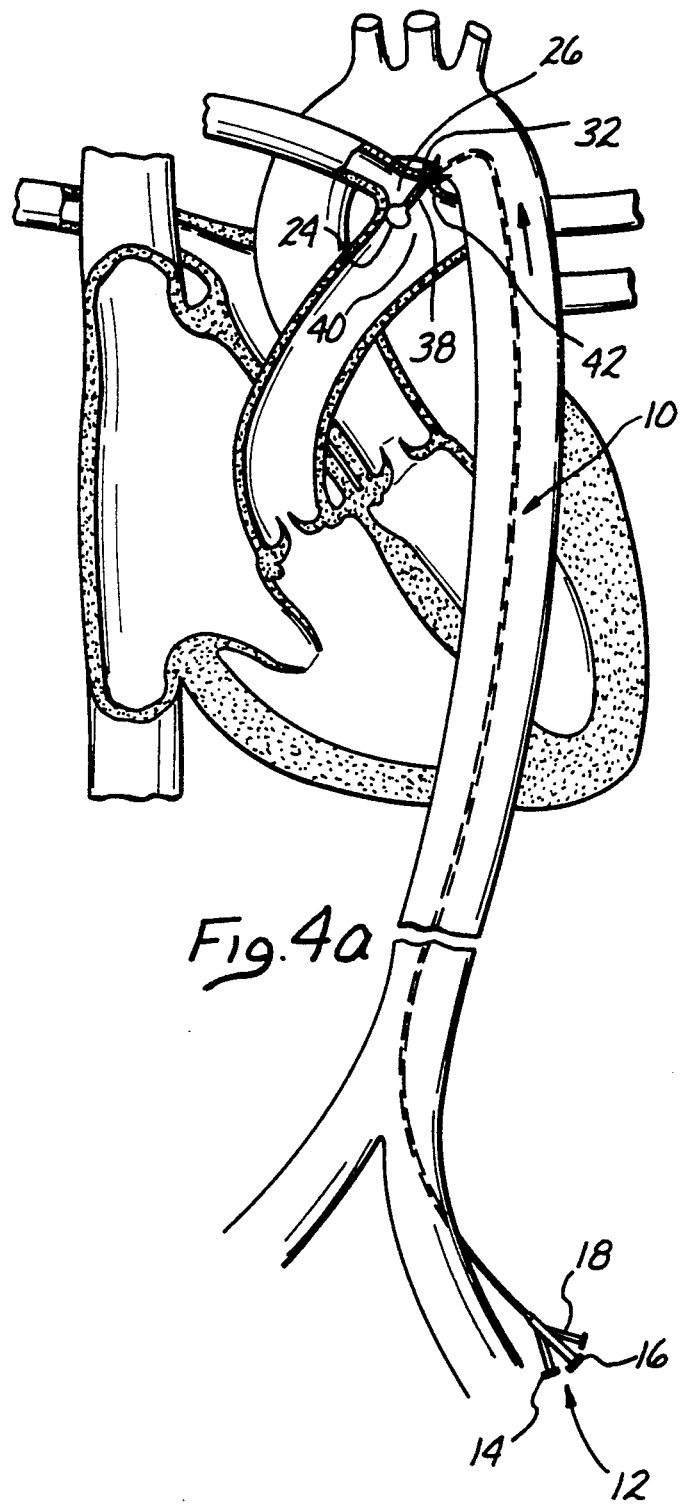
Fig. 1
Fig. 4a

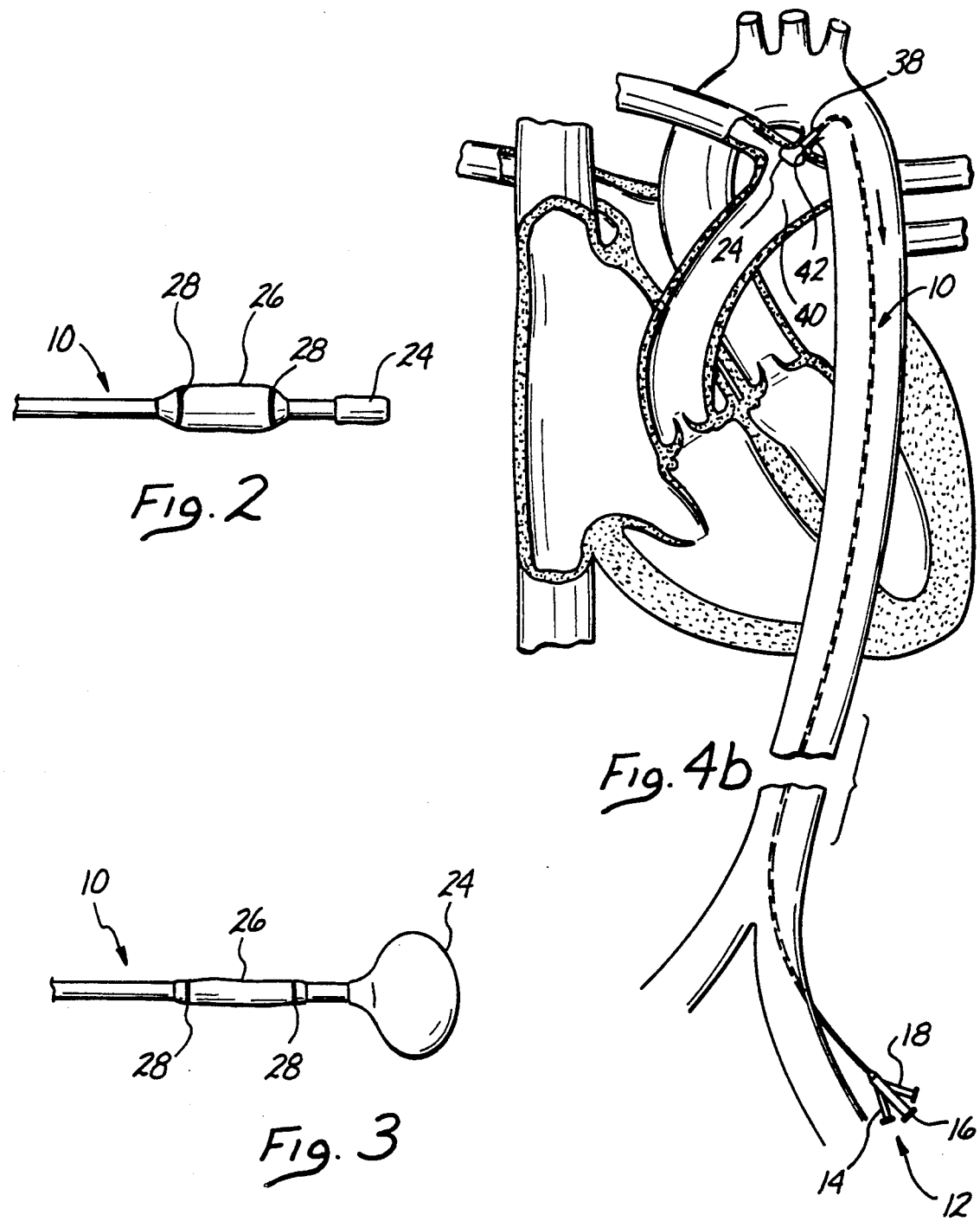

DOUBLE BALLOON PEDIATRIC DUCTUS ARTERIOSUS STENT CATHETER AND METHOD OF USING THE SAME

BACKGROUND OF THE INVENTION

1. Field of the Invention

The invention relates to the field of cardiac catheters and in particular to catheters used to place stents in infants and the methods by which such catheters may be used for pediatric stent placement.

2. Description of the Prior Art

Work began as early as 1969 using nonexpandable stainless steel coils in combination with angioplasty catheter techniques for the placement of stents in dog femoral arteries C. T. Dotter, *"Transluminally placed coil spring endarterial tube grafts: Long term patency in canine popliteal artery,"* Invest. Radiol 4:329–331 (1969). Following Dotter, several different types of stent designs were devised, but each of these designs suffer from limitations which prevented their success in clinical application. These limitations included bulky configurations that made delivery to target lesions difficult, unpredictable expansion of the device, migration due to stent-vessel mismatch, abrupt thrombosis, or gradual restenosis from intimal hyperplasia.

Evolving from these early efforts are three basic designs which include a spring-loaded stent, usually made of stainless steel and constrained to a small diameter on a delivery catheter. The stent is allowed to spring open to a predetermined diameter when the constraint is removed. See Sigwart et al. *"Intravascular stents to prevent occlusion and restenosis after transluminal angioplasty,"* N. Engl. J. Med. 316:701–706 (1987).

A second type of stent relies upon thermal expansion. Stents made of nitinol are initially configured as small diameter wires or coils and expand to predetermined shapes with the application of body heat.

A third type of stent is introduced with a balloon catheter. Stents of this type rely on plastic deformation of the metal caused by mechanical expansion when driven by a balloon. Woven stainless steel wire stents are crimped over conventional balloon catheters and then expanded after being positioned at the target site. When the balloon is inflated, the stent is embedded in the vessel wall. Following balloon deflation and removal, the stent remains in place, holding the vessel open if properly placed initially, Palmaz et al., *"Expandable intraluminal graft: Preliminary study"* Radiology 156:73–77 (1985); Palmaz et al. *"Expandable intraluminal grafting,"* Radiology 160:723–726 (1986); Palmaz et al. *"Expandable intraluminal vascular graft: A feasibility study,"* Surgery 99:199–205 (1986); Palmaz et al. *"Expandable intrahepatic portacaval shunt stents: Early experience in the dog"*, AJR 145:821–825 (1985). See also generally, Schatz, *"Introduction to intravascular stents,"* Interventional Cardiology Clinics Vol. 6 No. 3 pp 357–372 (1988); Palmaz, *"Balloon-expandable intravascular stent,"* AJR 150:1263–1269 (1988); O'Laughlin, *"Use of Endovascular Stents in Congenital Heart Disease,"* Circulation Vol. 83, 1923–39 (1991). However, each of these prior art catheters for delivering stents did so by means of a single balloon angioplasty catheter.

In a variety of congenital pediatric heart defects, there is a need for augmented pulmonary blood flow due to pulmonary atresia or stenosis. These defects include Tetralogy of Fallot, tricuspid atresia and complex forms of pulmonic stenosis. It is advantageous in these applications to maintain a patent ductus arteriosus. In other words, when blood circulation through an infant's heart is blocked or substantially restricted, blood flow from the heart to the lungs is diverted through the ductus arteriosus which is open in the infant's heart only for a relatively short period of time after birth. As the ductus arteriosus closes, as a result of normal heart development, no alternative path then remains to allow for adequate pulmonary circulation in the defective heart. In the worst cases, the infant will eventually become cyanotic and suffocate.

Conventional treatment includes drug treatments by infusions of prostaglandin which inhibits the closing of the ductus arteriosus. This treatment has a disadvantage that the infant must be kept on constant intravenous infusions of the drug until it has become large enough to survive cardiac surgery.

Ultimately, a pulmonary shunt, either through an artificial prosthetic, diversion by a Blalock-Taussig shunt, or central shunt must be performed. These latter procedures involve surgical intervention with inherent anesthesia and perioperative risks.

Therefore, it is desirable to evaluate perfected cardiac catheterization techniques to establish a systematic pulmonary artery communication. What has been attempted in the prior art is the placement of stents in the ductal arteriosus using conventional angioplasty catheters. See Coe, *"Redilating Ductal Stents in Newborn Lambs,"* 2163 Abstracts from 64th Scientific Sessions II-545; Moore et al., *"Use of an Intravascular Endoprosthesis (stent) to Establish and Maintain Short Term Patency of the Ductus Arteriosus in Newborn Lambs,"* JACC Vol. 17 No. 2 (1991); and Coe et al., *"A Novel Method to Maintain Ductal Patency,"* JACC Vol. 17 No. 2 (1991).

In Coe's study in newborn lambs, catheters were introduced via a cutdown in the neck under general anesthesia. A stainless steel stent which was securely mounted on a coronary angioplasty catheter, was introduced into the external jugular vein and manipulated through the right heart under fluoroscopy to place the balloon carefully in the ductus arteriosus. The position of the ductus was previously determined angiographically. The balloon on the catheter was inflated to release the stent in the ductus arteriosus without embolisation.

The difficulty with this technique, however, is proper placement in the ductus arteriosus which is a very small and short tubular shunt in the infant's cardiac circulation system near the heart. The stent, although made of stainless steel, is very thin and can be seen only with difficulty under fluoroscopy, which is the only means for determining when and if the stent is properly placed. Improper placement within the ductus arteriosus could result either in failure of the stent to maintain the ductus arteriosus open and/or possible creation of clotting site with resulting complications from embolism.

The inclusion of radiographic markers, either on the stent or the delivery catheter, helps determination of the location of the stent, but provides no assistance in determining whether or not the stent is properly placed with ductus.

Therefore, what is needed is an apparatus and method which can be used in combination with conventional fluoroscopy to allow accurate and secure placement of a stent in the ductus arteriosus of an infant.

BRIEF SUMMARY OF THE INVENTION

A cardiac catheter for use in maintaining the patency of the ductus arteriosus in infants is provided with two inflatable balloons, a distal end balloon and a stent balloon. Each balloon is independently inflatable. The stent is carried temporarily on the stent balloon and is delivered by the catheter to the site of the ductus arteriosus. Expansion of the stent balloon expands the stent and places it at the target site. The stent balloon is confidently and reliably placed in the ductus arteriosus by first inflating the distal end balloon and withdrawing the catheter until abuts the opening of the ductus arteriosus through which it has been previously disposed. When this abutment is realized, the stent balloon is necessarily positioned appropriately within the ductus arteriosus. While maintaining the inflation of the distal end balloon, the stent balloon is inflated and the stent placed. After placement, both the distal end balloon and stent balloon are deflated and the catheter withdrawn.

More precisely the invention is a catheter for use in maintaining patency of the ductus arteriosus with a stent comprising a catheter body having a proximal end and a distal end. An inflatable distal end balloon is disposed on the distal end of the catheter body. An inflatable stent balloon is disposed near the distal end of the catheter body proximate to the distal end balloon. A mechanism is provided for selectively inflating the distal end balloon and stent balloon. As a result, the stent disposed on the stent balloon is reliably and confidently positioned within the ductus arteriosus and installed therein.

In the illustrated embodiment the distal end balloon is generally spherical when inflated. Whatever shape is chosen for the distal end balloon, it has a shape and size such that, when the distal balloon is inflated, it cannot be withdrawn through the ductus arteriosus.

The stent balloon is generally cylindrical in shape when inflated. The stent balloon has a longitudinal length along the axis of the cylindrical shape approximately equal to the stent.

The stent balloon may further comprise a radiographic opaque marker at one end of the stent balloon, or a pair of radiopaque markers, one marker at each end of the stent balloon.

The mechanism for selectively inflating the distal end balloon and the stent balloon comprises a corresponding plurality of ports communicated through the catheter body. The ports are disposed at the proximal end of the cathether body and communicated through the catheter body to the distal end balloon and stent balloon at or near the distal end of the catheter body.

The catheter may further include an element for communicating with the distal end of the catheter body from the proximal end of the catheter body. The element for communicating comprises a port disposed at the proximal end of the catheter body. A lumen is disposed through the catheter body and a distal end port is defined at the distal end of the catheter body.

The invention is also a method of delivering a stent to the ductus arteriosus of an infant comprises the steps of providing a catheter having a catheter body with a proximal and distal end. The distal end is provided with an inflatable distal end balloon and proximate thereto an inflatable stent balloon. A stent is disposed on the stent balloon so that the stent is temporarily secured to the catheter. The distal end is disposed through the ductus arteriosus of the infant. The distal end is disposed completely through the ductus arteriosus into an adjacent artery. The distal end balloon is then inflated. The distal end of the catheter is then withdrawn through the ductus arteriosus until the distal end balloon abuts the opening of the ductus arteriosus to thereby prevent further withdrawal. The stent balloon is inflated while maintaining the distal end balloon in an inflated condition and in abutment to the opening of the ductus arteriosus. The inflating stent balloon disposes the stent in the ductus arteriosus. The stent balloon and the distal balloon are then deflated. The catheter is finally removed from the ductus arteriosus. As a result, the stent is confidently and reliably delivered and disposed to the ductus arteriosus.

The method further comprises the steps of providing the stent balloon with at least one radiographic opaque marker to delineate an end of the stent balloon, and observing the radiographic opaque marker under fluoroscopy to corroborate disposition of the stent within the ductus arteriosus.

The step of providing the stent balloon with a radiographic opaque marker comprises the step of providing the stent balloon with separate radiographic opaque markers at each end of the stent balloon.

The step of inflating the distal end balloon inflates the distal end balloon to a size and shape which prevents its withdrawal through the ductus arteriosus.

The step of inflating the distal end balloon and the stent balloon inflates the balloons through ports provided at the proximal end of the catheter.

Now it can be understood that in general terms the invention is a catheter for maintaining the patency of the ductus arteriosus with a stent in an infant comprising a positioning element for physically determining the position of the catheter within the ductus arteriosus of the infant. A delivery element disposes the stent in the ductus arteriosus to maintain its patency. As a result, the stent is confidently and reliably disposed in the ductus arteriosus without regard to fluoroscopic visibility.

The positioning element comprises a selectively actuatable element configurable into a uniquely determined position relative to position to the ductus arteriosus.

The selectively activatable element is disposed on a distal end of the catheter and is selectively activated when the distal end is disposed through and beyond the ductus arteriosus. The element then is configured after activation to the uniquely determined position relative to the ductus arteriosus.

The delivery element is independently operable from the positioning element. The delivery element comprises a stent for disposition within the ductus arteriosus. The stent is temporarily fixed to the delivery element and is selectively disposed within the ductus arteriosus by activation of the delivery element.

The invention may better visualized by now turning to the following drawings wherein like elements are referenced by like reference numerals.

BRIEF DESCRIPTION OF THE DRAWINGS

FIG. 1 is a side view of a delivery catheter of the invention used for placement of stents within the ductus arteriosus of an infant.

FIG. 2 is a side view of the distal end of the catheter of FIG. 1 shown in enlarged scale with the stent balloon in an inflated condition.

FIG. 3 is a side view of the distal end of the catheter as shown in FIG. 2 but with the distal end balloon inflated instead of the stent balloon.

FIG. 4a is a simplified cross-sectional view of an infant's heart showing the catheter of FIGS. 1-3 inserted through the ductus arteriosus and with the distal balloon inflated prior to delivery of the stent.

FIG. 4b is a simplified cross-sectional view of FIG. 4a showing the distal end properly positioned in the ductus arteriosus and with the stent balloon inflated to deliver the stent.

The invention and its various embodiments may now be better understood by turning to the following detailed description.

DETAILED DESCRIPTION OF THE PREFERRED EMBODIMENTS

First the various major elements of the catheter of the invention will be briefly identified. Cardiac catheter 10, as shown in side view of FIG. 1 in the illustrated embodiment, illustrates that the proximal end 12 is fitted with three ports 14, 16 and 18. Ports 14, 16 and 18 are merged into a catheter body 20 through conventional techniques and are coupled to elements at the distal end 22 of catheter 10 described below.

Distal end 22 of catheter 10 has a distal end balloon 24 and behind balloon 24 is a stent balloon 26. Distal balloon 24, when inflated as shown in FIG. 3 in the illustrated embodiment has a diameter of approximately 10 millimeters and is generally spherical or oblate.

Stent balloon 26 in the illustrated embodiment has a length of 7-10 millimeters to form a generally cylindrical balloon of 3-4 millimeters in diameter. Stent balloon 26 in one embodiment includes radiographic markers 28 at each end of stent balloon 26 to enhance its fluoroscopic visibility. FIG. 2 shows in enlarged view stent balloon 26 in an inflated condition with distal balloon 24 deflated. FIG. 3 shows the opposite configuration, namely stent balloon 26 deflated and distal balloon 24 inflated.

Returning to FIG. 1, catheter 10, which in the preferred embodiment is approximately 60 centimeters in length, communicates port 14 with distal balloon 24. Port 18 is communicated with stent balloon 26. The central port 16 is optionally provided with a hemostasis valve for an end port 30 through distal end 22 of catheter 10 to allow infusions to be injected and specimens to be withdrawn, if desired. In addition, central port 16 may provide access for a guidewire to assist in positioning distal tip 22 within the ductus arteriosus.

The number of lumens within catheter 10 may cause catheter 10 to be relatively flexible. In such an event, the use of a conventional catheter guide tube (not shown) may be telescopically disposed around catheter 10 and used to guide catheter 10 toward its proper target site. Alternatively, the central lumen and corresponding port 16 may be eliminated along with end port 30 to provide for a stiffer catheter, which may be manipulated without the use of a catheter guide tube.

Distal balloon 24 and stent balloon 26 are inflated through ports 14 and 18 respectively by conventional means, namely inflation by air or by fluid through a syringe or pump.

Turn now to FIGS. 4a and 4b which illustrate the placement of catheter 10 within the ductus arteriosus 32 of an infant's heart 34. Catheter 10 is inserted in the illustrated embodiment through a femoral incision point in femoral artery 36. Using conventional techniques under fluoroscopy, the distal end 22 is guided into ductus arteriosus 32 with both balloons 24 and 26 in a noninflated configuration. While radiopaque markers 28 assist in the ease of identification of a stent 38, which has been placed over stent balloon 26 and manually crimped thereon to temporarily secure it, the exact placement of stent 38 relative to ductus arteriosus 32 cannot be accurately and confidently determined under fluoroscopy. Its disposition through the ductus arteriosus is confidently known, but whether it has the correct longitudinal placement within the ductus arteriosus does not show up with reliability under fluoroscopic techniques notwithstanding the existence of radiographic markers 28.

With distal end 22 confidently placed into ductus arteriosus 32, it is inserted well into and through the ductus arteriosus 32 to a point where the surgeon is also confident that distal end 22 has been extended into artery 40 as shown in FIG. 4a.

At this point, distal end balloon 24 is inflated through port 14 and while the inflation is retained, catheter 10 is withdrawn until end balloon 24 abuts the opening 42 to ductus arteriosus 32 as shown in FIG. 4b. At the point of abutment, distal balloon 24 prevents further withdrawal of distal end 22 of catheter 10 through ductus arteriosus 32. Inasmuch as stent balloon 26 is only one to three millimeters behind the attachment of distal balloon 24 to distal end 22 of catheter 10, appropriate placement of stent 38 within ductus arteriosus 32 is physically guaranteed regardless of what may or may not be visually observable under standard fluoroscopy.

Once the surgeon then feels abutment of distal balloon 24 within ductus arteriosus 32, stent balloon 26 is then inflated, expanding stent 38 in ductus arteriosus 32. After the appropriate expansion of stent 38 has been achieved, both balloons 24 and 26 are then deflated and catheter 10 removed. In some cases, if it is later determined that ductus arteriosus has not been opened sufficiently by stent 38 or becomes subject to constriction for any reason, catheter 10 may be reinserted and confidently repositioned as described above with reinflation of stent balloon 26 to reexpand or clear ductus arteriosus 32.

An example of the use of the invention will help to illustrate its methodology. An experimental animal study was performed using neonatal lambs which were less than 48 hours old. The lambs were sedated, anesthetized and prepared for catheterization. The jugular vein or femoral artery were cannulated percutaneously or via cutdown. Prostaglandin (PGE) was infused to maintain the ductus arteriosus patent. Both right and left heart catheterization was performed using sterile techniques under fluoroscopic guidance. Radiopaque contrast was injected into the aorta to demonstrate the ductus arteriosus.

The stent delivery catheter of the invention was advanced from the femoral artery to the ductus arteriosus. The distal latex balloon was expanded within the pulmonary artery. The catheter was then drawn back through the ductus arteriosus. Because the expanded distal latex balloon cannot be drawn into the smaller ductus arteriosus, it prevented the catheter from being withdrawn any further. At that point, the adjacent, proximal angioplasty stent balloon was inflated to five atmospheres pressure to expand the stent and lodge it within the ductus arteriosus. Both balloons were then rapidly deflated and the catheter withdrawn. The aortagram, right and left heart catheterizations, were then repeated. The catheters were all removed with skin incisions sutured.

Precautions were taken to prevent dislodgment of the stent from the delivery catheter prematurely by advancing the entire catheter-stent assembly through a sheath to the side of ductus arteriosus or alternatively by crimping the stent onto the balloon.

Subsequent observation of the lambs was made for growth, signs and symptoms of heart failure. Periodic echocardiographic evaluation of the patency of the stented ductus arteriosus was performed. In each case, successful stent placement without deleterious effects was observed. Subsequent dissection was made to allow growth inspection and microscopy for a thrombus formation, obstruction, endothelialzation, evidence of damage to the aorta, pulmonary artery and ductus arteriosus as well as evaluation of the accuracy of the stent placement. Again no deleterious effects were found and placement was found to be reliable and accurate in each occasion.

Catheterization was repeated prior to dissection to evaluate hemodynamics including relative pulmonary to systematic flow and pulmonary pressures. Again, expected in normal hemodynamics was observed.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

I claim:

1. A catheter for use in maintaining patency of the ductus arteriosus comprising:
   a catheter body having a proximal end and a distal end;
   an inflatable distal end balloon disposed on said distal end of said catheter body;
   an inflatable stent balloon disposed near said distal end of said catheter body proximate to said distal end balloon;
   means for selectively inflating said distal end balloon and stent balloon; and
   an expandable and permanently implantable stent disposed on said stent balloon, said expandable stent assuming a permanent expanded configuration upon inflation of said stent balloon,
   whereby said stent disposed on said stent balloon is adapted to be reliably and confidently positioned within said ductus arteriosus and installed therein.

2. The catheter of claim 1 wherein said distal end balloon is generally spherical when inflated.

3. The catheter of claim 1 wherein said distal balloon has a shape and size such that, when said distal balloon is inflated, it assumes a predetermined size, said predetermined size being greater than said ductus arteriosus.

4. The catheter of claim 1 wherein said stent balloon is generally cylindrical in shape when inflated.

5. The catheter of claim 4 wherein said stent balloon has a longitudinal length along the axis of said cylindrical shape approximately equal to said stent.

6. The catheter of claim 1 wherein said stent balloon further comprises a radiographic opaque marker at one end of said stent balloon.

7. The catheter of claim 6 wherein said stent balloon has a pair of radiopaque markers, one marker at each end of said stent balloon.

8. The catheter of claim 1 wherein said means for selectively inflating said distal end balloon and said stent balloon comprises a corresponding plurality of ports communicated through said catheter body, said ports being disposed at said proximal end of said catheter body and communicated through said catheter body to said distal end balloon and stent balloon at or near said distal end of said catheter body.

9. The catheter of claim 1 further comprising means for communicating with said distal end of said catheter body from said proximal end of said catheter body.

10. The catheter of claim 9 wherein said means for communicating comprises a port disposed at said proximal end of said catheter body, a lumen being disposed through said catheter body and a distal end port being defined at said distal end of said catheter body.

11. A method of delivering a stent to the ductus arteriosus of an infant comprising the steps of:
    providing a catheter having a catheter body with a proximal and distal end, said distal end being provided with an inflatable distal end balloon and proximate thereto an inflatable stent balloon;
    disposing a stent on said stent balloon so that said stent is temporarily secured to said catheter;
    disposing said distal end through said ductus arteriousus of said infant, said distal end being disposed completely through said ductus arteriosus into an adjacent artery;
    inflating said distal end balloon;
    withdrawing said distal end of said catheter through said ductus arteriosus until said distal end balloon abuts the opening of said ductus arteriosus to thereby prevent further withdrawal;
    inflating said stent balloon while maintaining said distal end balloon in an inflated condition and in abutment to said opening of said ductus arteriosus, said inflating stent balloon disposing said stent in said ductus arteriosus;
    deflating said stent balloon and said distal balloon; and
    removing said catheter from said ductus arteriosus,
    whereby said stent is confidently and reliably delivered and disposed to said ductus arteriosus.

12. The method of claim 11 further comprising the steps of providing said stent balloon with at least one radiographic opaque marker to delineate an end of said stent balloon, and observing said radiographic opaque marker under fluoroscopy to corroborate disposition of said stent within said ductus arteriosus.

13. The method of claim 12 wherein said step of providing said stent balloon with a radiographic opaque marker comprises the step of providing said stent balloon with separate radiographic opaque markers at each end of said stent balloon.

14. The method of claim 11 where said step of inflating said distal end balloon inflates said distal end balloon to a size and shape which prevents its withdrawal through said ductus arteriosus.

15. The method of claim 11 where in said step of inflating said distal end balloon and said stent balloon, said balloons are inflated through ports provided at said proximal end of said catheter.

16. A catheter for maintaining the patency of the ductus arteriosus in an infant comprising:

positioning means for physically determining the position of said catheter, said positioning means being adapted to determine said position of said catheter within said ductus arteriosus of said infant;

an expandable and implantable stent capable of assuming a permanent expanded configuration; and delivery means for disposing and configuring said stent in said ductus arteriosus to permanently maintain its patency, whereby said stent is adapted to be confidently and reliably disposed in said ductus arteriosus without regard to fluoroscopic visibility.

17. The catheter of claim 16 wherein said positioning means comprises a selectively actuatable element configurable into a uniquely determined position relative to position to said ductus arteriosus.

18. The catheter of claim 17 wherein said selectively activatable element is disposed on a distal end of said catheter and is selectively activated when said distal end is disposed through and beyond said ductus arteriosus, said element then being configured after activation to said uniquely determined position relative to said ductus arteriosus.

19. The catheter of claim 16 wherein said delivery means is independently operable from said positioning means.

20. The catheter of claim 16 wherein said delivery means comprises a stent adapted for disposition within said ductus arteriosus, said stent being temporarily fixed to said delivery means and adapted to be selectively disposed within said ductus arteriosus by activation of said delivery means.

* * * * *